Figure 4:
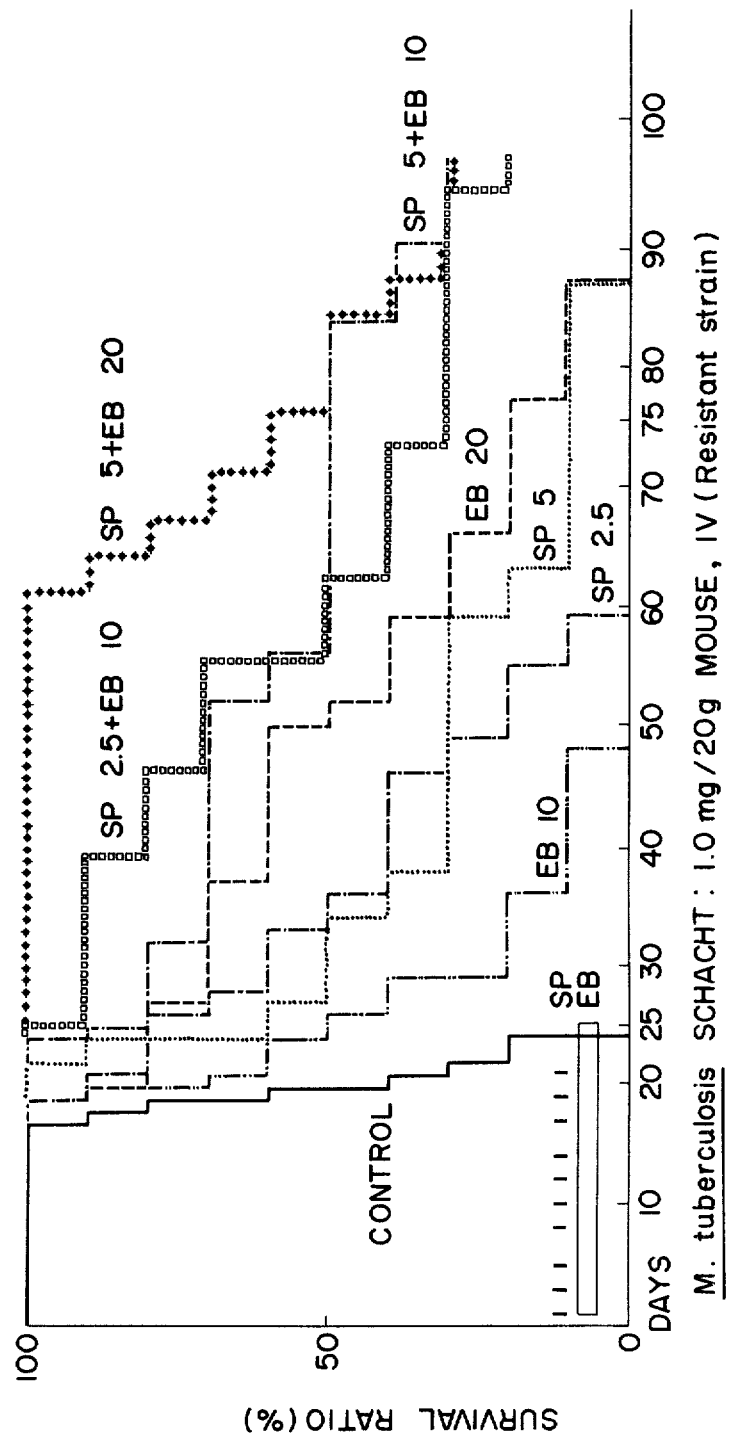

United States Patent [19]

Komatsu et al.

[11] 3,943,247

[45] Mar. 9, 1976

[54] TREATMENT OF BACTERIAL INFECTIONS WITH GLUCAN COMPOSITIONS

[75] Inventors: Nobuhiko Komatsu; Sumio Sakai; Gosaku Saito; Syoichi Kikumoto; Keitaro Kimura, all of Tokyo, Japan

[73] Assignees: Kaken Kagaku Kabushiki Kaisha; Taito Co., Ltd., both of Japan

[22] Filed: July 11, 1973

[21] Appl. No.: 378,054

Related U.S. Application Data

[63] Continuation-in-part of Ser. No. 255,682, May 22, 1972, Continuation of Ser. No. 37,029, May 13, 1970, abandoned, which is a continuation-in-part of Ser. No. 766,630, Oct. 10, 1968.

[52] U.S. Cl. ............................................. 424/180
[51] Int. Cl.² ...................................... A61K 31/70

[58] Field of Search ................................. 424/180

[56] References Cited
UNITED STATES PATENTS 3,301,848   1/1967   Halleck ............................. 260/209

*Primary Examiner*—Jerome D. Goldberg
*Assistant Examiner*—D. W. Robinson
*Attorney, Agent, or Firm*—Bucknam and Archer

[57] ABSTRACT

Prevention and therapeutics of bacterial infections based on the activation of the reticuloendothelial system with glucan having $\beta$-1, 3-linkage in the main chain, the derivatives and partially hydrolysed product thereof.

5 Claims, 5 Drawing Figures

FIG. 1-a

PHAGOCITIC ACTIVITY OF THE GLUCAN AND ZYMOSAN BY USING CARBON CLEARANCE METHOD 2 mg (about 100 mg/kg) of Zymosan was injected ip in mouse 4 and 2 day before iv injection of pelikan ink (16 mg/ml/100 g body weight)

Turbidity (optical density) was measured at 660 nm.

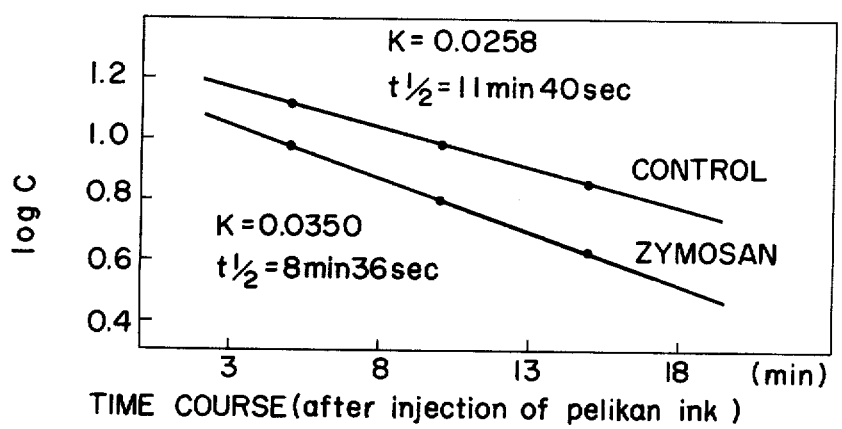

FIG. 1-b 0.05 mg (about 2.5 mg/kg) of the glucan was injected ip in mouse 4 and 2 day before iv injection of pelikan ink (20 mg/ml/100 g body weight)

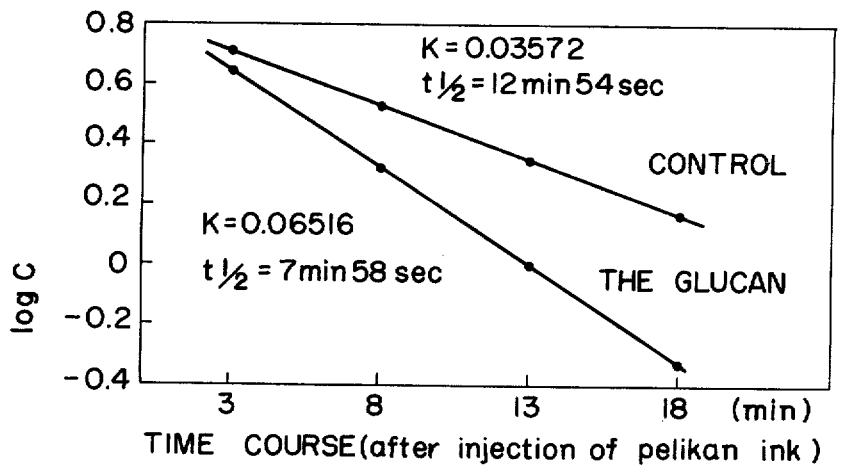

$K = (\log C_1 - \log C_2) / T_2 - T_1$

K : Clearance index $C_1$ and $C_2$ : Concentration of pelikan ink at the time $T_1$ and $T_2$ respectivly t 1/2 : Half time

FIG. 2

EFFECT OF THE GLUCAN ON PHAGOCYTIC ACTIVITY IN VITRO

Saccharomyces cerevisiae ATCC 9763 ($1.3 \times 10^7$/ml)

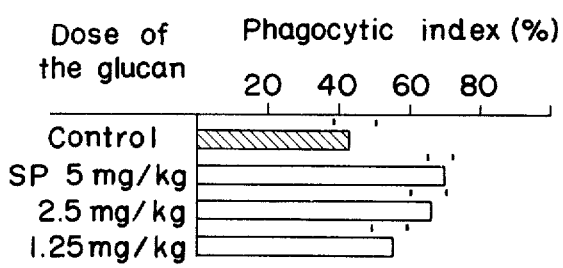

Candida albicans YU 1200 ($7.8 \times 10^6$/ml)

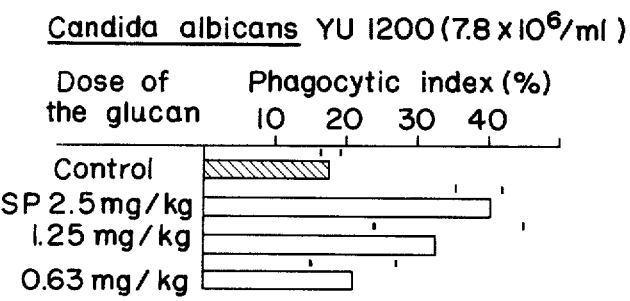

The glucan

Before 2,4,6 days, Ip
Mouse
  dd, mole 25-30 gr.
Phagocytes
  Peritoneal macrophages
  $2-4 \times 10^6$
Phagocytised time
  Saccharomyces 30 min
  Candida 8 min
Staining
  Giomsa stain 20 min.
  (37°C)
Phagocytic index
  Phagocytioing macrophage
  numbers per
  100 phagocytes

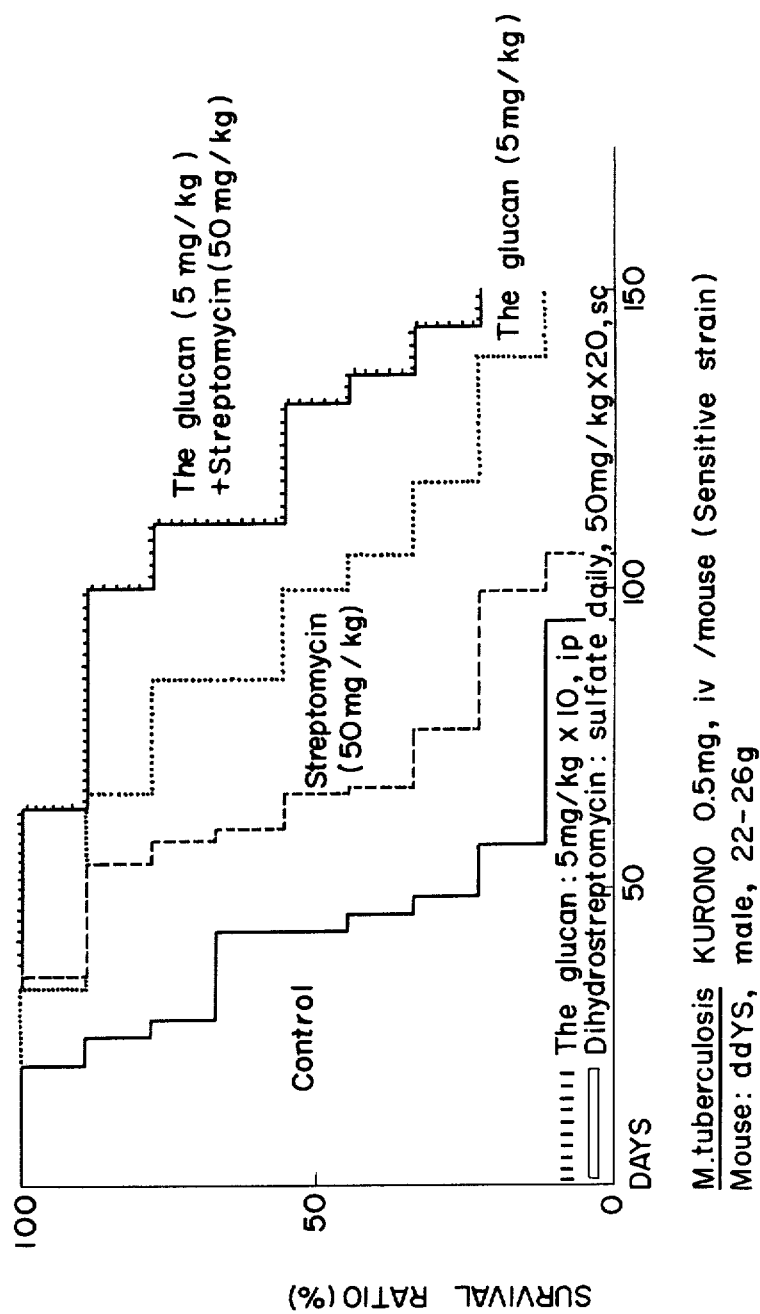

COMBINED TREATMENT OF EXPERIMENTAL TUBERCULOSIS WITH THE GLUCAN AND OTHER ANTITUBERCULOUS DRUGS

TREATMENT OF BACTERIAL INFECTIONS WITH GLUCAN COMPOSITIONS

This application is a continuation-in-part of Ser. No. 255,682, filed May 22, 1972, which is the continuation of Ser. No. 37029, filed on May 13, 1970, which was a continuation-in-part application of Ser. No. 766,630 filed Oct. 10, 1968, the latter having now been abandoned Ser. No. 37,029 has now been abandoned.

The present invention relates to a method for the prevention and for the therapeutics of bacterial infections in man and animals based on the activation of the reticuloendothelial system by a glucan having $\beta$-1, 3-linkage in the main chain, the derivatives and partially hydrolysed product thereof.

An object of this invention is to prevent and treat various bacterial infectious diseases in man and animals by administration of the glucan of this invention, the derivatives and partially hydrolysed products of the glucan by stimulation of the phagocytic activity of the reticuloendothelial cells. Another object of this invention is to increase the therapeutic activity of antibiotics by combination with the same glucan, its derivatives and its hydrolyzed products.

The glucans, which are the subject matter of the present invention, are polymers of linearly $\beta$-(1 → 3)-linked D-glucopyranose residues having side chains at various intervals thereon, each of the said side chains comprising one mole of $\beta$-(1 → 6)-linked D-glucopyranose residue. The general structure of the glucans is as follows:

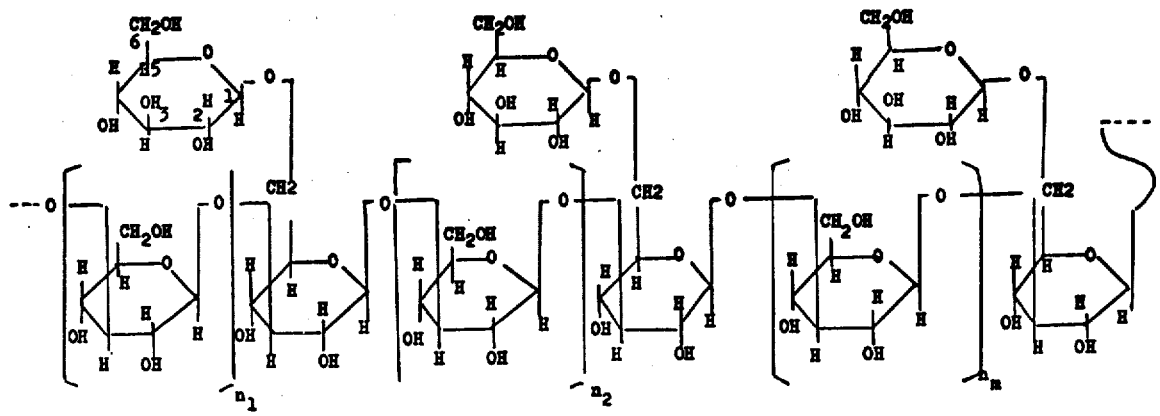

wherein G represents a $\beta$-D-glucoopyranose residue, the indicia 1, 3 and 6 indicate the positions where adjacent glucose residues are linked, each [$3^G1$] unit representing linearly $\beta$-(1 → 3)linked D-glucopyranose residues, and each of $n_1 \ldots n_m$ is the number of said linearly linked glucose residues in each [$3^G1$] unit, said $n_1 \ldots n_m$ being independently a number from 0 to about 10.

Thus the general structure of the glucans is as follows, with the structure for each G being shown in conventional form and the numbering of one of the pyranose rings being indicated:

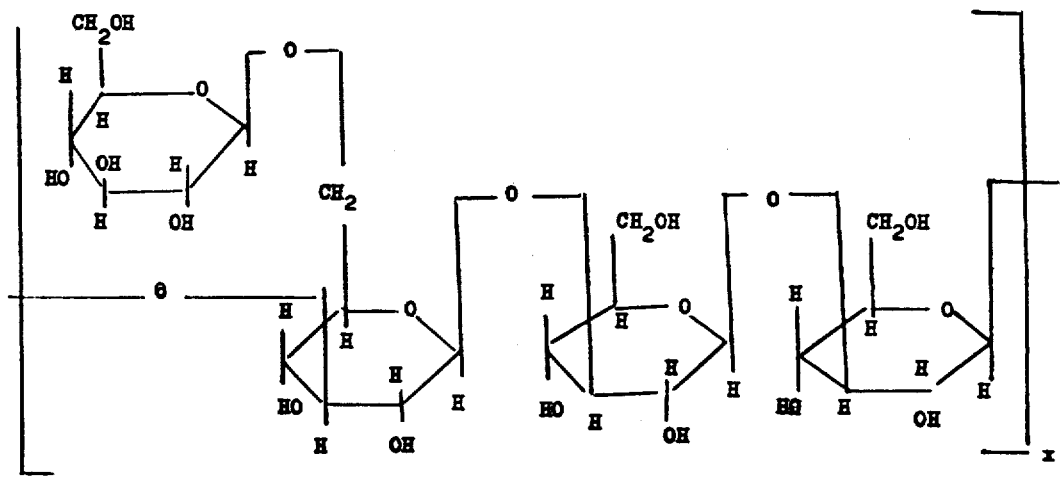

wherein $n_1, n_2, - - - n_m$ are as defined above. For a better understanding, by way of example, a glucan in which all $n$ are 2 is shown as follows:

where $x$ is more than 3.

As is known, glucans of the above formula can be obtained from various fungi. It has now been found that a large number of fungi belonging to the following strains also produce the glucans having the action described above.

A. Ascomycetes:
Chaetomium cochliodes
Cochliobolus sativus
Ophiobolus miyabeanus
Pyrenophora teres
Sclerotinia arachidis
Sclerotinia mali

*Sclerotinia sclerotiorum*
B. Basidiomycetes:
*Corticium centrifugum*
*Flammulina velutipes*
*Lentinus edodes*
*Lindera bicolumnata*
*Melanoleuca verrucipes*
*Pholiota nameko*
*Russula emetica*
*Russula sororia*
*Scleroderma cepa*
C. Fungi imperfecti:
*Alternaria kikutiana*
*Cercospora cryptomeriae*
*Cladosporium fulvum*
*Myrothecium verrucaria*
*Sclerotium tuliparum*
*Sclerotium hydrophylum*

The strains previously reported as producing such glucans are *Sclerotinia libertiana* (M. Kitahara et al.: J. Agr. Chem. Soc. Japan, 35, 468,474 (1961)), *Sclerotium glucanicum*, *Sclerotium delphinii*, *Sclerotium rolfsii*, *Sclerotium coffeicolum*, *Corticium rolfsii*, *Sclerotinia gladoli*, and *Stromatinia narcissi* (F. E. Halleck: U.S. Pat. No. 3,301,848), *Schizophyllum commune* (S. Kikumoto et al: Taito Kenkyusho Hokoku, 22, 77 (1964), 23, 77 (1965), Japanese Pat. No. 505,408), *Claviceps purpurea*, and *Claviceps fusiformis* (A. S. Perlin et al.: Can. J. Chem., 41, 2278 - 82 (1963), and K. Buck et al.: J. Gen. Microbiol., 51, 337 (1968)). Some of these glucans are useful as additives in the paper industry and as noncaloric stable gelling agents in the food industry. Some of the derivatives of the glucan which are active within the scope of the present invention are the methylether, the carboxymethylether, the diethylaminoethylether, the acetylester, the sulfonylester and the phosphoric acid ester. Jert-hydrolyzed products are obtained from the said glucan by treatment with $\beta$- 1, 3 - glucans, acids and alkalies.

According to the present invention, it has been found that pharmaceutical preparations of this glucan and the derivatives thereof significantly stimulate the function of the reticuloendothelial system, and cause acceleration of phagocytic activity of phagocytes. This type of activity is a very characteristic pharmacological function of the glucan against a living body. This activity can be proved by the test for reticuloendothelial function by intravenous injection of Pelikan ink into mice and measuring its clearance by blood level. It has been clearly indicated by this test that intraperitoneal injection of about 2.5 mg/kg of the glucan results in acceleration of the reticuloendothelial system function. In another test, about 2.5 mg/kg of this glucan was administered intraperitoneally to mice every other day for three times, the peritoneal macrophages were collected, and these macrophages were mixed in vitro with a definite number of cells of *Saccharomyces cerevisiae* and *Candida albicans*. After 30 and 8 minutes, respectively, the cells were stained with Giemsa and their phagocytic index (= number of phagocytising macrophage/100 phagocytes) was measured. This result indicated that the phagocytic activity of the reticuloendothelial cells had been accelerated about two fold.

Administration of the glucan of this invention in mice results not only in acceleration of phagocytic activity, but also in elevation of the activity of various enzymes in the peritoneal macrophage, and helps in efficient digestion of foreign matter. The form of the macrophage grew large and its acid phosphatase staining showed the presence of numerous acid phosphatase-positive vacuoles and lysosome granules, indicating the functional activation.

This acceleration of the phagocytic activity is manifestly effective against some bacterial infectious diseases.

Preventive tests on various infectious diseases in mice which had been infected not only with pathogenic bacteria like *Staphylococcus aureus*, *Klebsiella pneumoniae*, *Escherichia coli*, *Proteus vulgaris*, *Pseudomonas aeruginosa*, and *Mycobacterium tuberculosis*, but also with pathogenic fungi like *Candida albicans* were carried out and survival of the infected and control mice was examined. Intraperitoneal injection of 1.25-5 mg/kg or intramuscular or subcutaneous injection of 20-100 mg/kg of the glucan of this invention resulted in a marked prolongation of the life of the infected mice.

Since the glucan of this invention does not show any antibacterial activity in vitro against these bacteria antibiotics. fungus, it is clear that its effect is due to a mechanism entirely different from that of antibiotics and, moreover, the effective dose is comparable to that of known anitbiotics.

The therapeutic activity of antibiotics is further increased by the combined treatment with the glucan of this invention. This fact is especially important in the case of diseases which progress chronically such as tuberculosis, in which appearance of side effect of antibiotics or chemopherapeutics on the nervous sytem and other functions of the body is observed rather often. This is due to the fact that the use of the glucan of this invention with antibiotics or synthetic antituberculous agents, such as streptomycin, ethambutal, and isonicotinic acid hydrazide, is able to reduce the dose of these antituberculous agents and consequently the side effects above described are reduced.

In diseases progressing chronically other than tuberculosis like the infection with Pseudomonas aeruginosa, so far no effective antibiotic of low toxicity is known and the antibiotic with strong side effects, Gentamycin, has to be used. In this case, combined dose of the glucan of this invention with a chemotherapeutics will enable the administration of smaller doses of Gentamycin resulting in reduction of its side effect.

It is well known that the present trend for a wide and frequent use of antibiotics has resulted in the marked appearance of resistant strains. Since the mechanism of action of the glucan of this invention resides in an increase of the phagocytic activity of the host, a specific feature of this glucan is that it is effective against either the resistant or sensitive strains of bacteria.

The toxicity of the glucan of the present invention is extremely low as in general with other polysaccharides. Various tests on rats given 1, 5, or 25 mg/kg of this glucan once daily intraperitoneally for one and three months showed no abnormality in increase of body weight, blood picture, weight of internal organs, and various biochemical tests on serum and urine, except for an increase of $\gamma$-globulin in serum which is not an ill effect, and splenomegaly observed in a group given 25 mg/kg. The characteristic point is the marked increase of reticuloendothelial cells in the spleen, lymph nodes, and the liver by histopathological examination. The fact indicates that the glucan of the present invention is effective in increasing phagocytic activity and accordingly advantageous against infectious diseases.

The glucan of the present invention did not show any antigenicity when examined by several immunological techniques.

The glucans of the present invention are dissolved in physiological saline and other physiologically tolerated vehicles such as the Ringer's or aqueous glucose solution. The preparations are usually administered intravenously, intramuscularly, subcutaneously, or intraperitoneally into hosts. The dosage of this glucan to a host differs according to the degree of the disease, and also according to the route of administration since the rate of diffusion from the site of administration differs accordingly. In general, the dose of the glucan of this invention is from 0.001 to 100 mg/kg/day.

The glucan of the present invention can be obtained by the following various methods.

a. Preparation from the liquid culture of mycelium:

This method comprises cultivation of mycelium of fungi in an appropriate liquid medium to produce glucans, and isolation and purification of said glucans through appropriate procedures. The culture medium may be either natural or synthetic.

The mycelium of fungi is inoculated in liquid medium, which is thereafter cultured as usual in a vessel such as a shaking flask, jar fermentor, or tank at 25° – 30°C, for 5 to 10 days. A supernatant freed from the mycelium by a suitable procedure such as filtration or centrifugation, is mixed with a suitable amount of an organic solvent miscible with water, such as methanol, ethanol, propanol, and acetone, to obtain glucans as a flocculent precipitate. If necessary, further purification by treatment with activated carbon, granular activated carbon or bone-char, and treatment with ion-exchange resins or dialysis and successive treatment with an increasing concentration of a solvent miscible with water yields white fibrous glucan. Glucan thus obtained is crushed and sieved to individual use. In some cases, of course, some of the above techniques may be omitted. The yield differs from fungus to fungus.

B. Preparation from capsule polysaccharide of fruit body of fungi:

Many fungi, involving mostly Basidiomycetes, are covered with a mucous capsule on their surface. For example, capsule polysaccharides of *Pholiota nameko*, *Pholiota adiposa*, etc., can be easily extracted with cold or warm water. Precipitation and purification to recover glucan from the aqueous extract are carried out according to the method (a) mentioned above.

C. Preparation from fruit body, sclerotium, and mycelium:

Using cold, warm, or hot water, or a few per cent of trichloroacetic acid solution, and a few per cent alkali solution, glucans can be easily extracted from mycelia. In such cases, it is desirable to homogenize fungi thoroughly.

Precipitation and purification to recover glucan from the extract are carried out according to the above mentioned (A).

The resulting glucans are usually grayish or white and fibrous, tasteless and odorless, and soluble in water, and highly viscous when they are in aqueous solution.

The facts that by the action of an exo-$\beta$-(1-3)-glucanase (E. T Reese et al.: Can. J. Microbiol., 5, 173 (1959); Y. Satomura et al.: Agr. Biol. Chem. (Tokyo), 25, 19 (1961) the glucan utilized in the present invention is easily hydrolysed to yield glucose and gentiobiose, and that after the Smith degradation (J. K. Hamilton, F. Smith: J. Am. Chem. Soc., 78, 5907 (1956), the same enzymic treatment produces glucose alone, indicate that the glucans have the structure mentioned hereinabove.

The methylether, carboxymethylether, diethylaminoethylether, acetylester, sulfonylester, and phosphorylester derivatives may be obtained by conventional methods, and partially hydrolyzed products may be obtained from the said glucan by treatment with enzymes, acids and alkalis.

The glucans of the present invention are difficult to prepare in an aqueous solution of higher concentration because of their high viscosity, and therefore, it is desirable to use them in a form of less than 0.5% aqueous solution. Furthermore, for the preparation of a composition suitable for medicinal use, it is necessary to add gradually glucan which is ground as fine as possible into a solvent with violent stirring for complete dispersion, and to continue the stirring until complete dissolution is obtained. In these cases, the use of a high-speed blender is preferable. The above procedures need to be carried out quite carefully, since when any lump is formed it is very difficult to dissolve completely.

The following examples are provided by way of illustration, and are not intended to limit this invention, the scope of which is indicated by the appended claims.

EXAMPLE 1

Preparation of the glucan.

Humfeld's basal medium (T. Sugihara and H. Humfeld: Applied Microbiol., 2 (3), 170, 1954) was mixed with 3% of glucose, 0.3% of urea, and 1 $\mu$g/ml of thiamine hydrochloride, the volume thereof was made to 1 liter and pH was adjusted to 4.50. Each 100 ml of the resulting medium was poured into a series of 500-ml Sakaguchi flasks. After sterilization at 120°C. for 15 minutes, each flask was inoculated with one loopful of *Schizophyllum commune* (T-189 strain) and cultivated on a reciprocal shaker at 28°C for seven days. After completion of fermentation, the culture broth was centrifuged at 8000 rpm for 5 minutes to remove the mycelium, the supernatant thus obtained was decolored with 0.05% of activated carbon, and filtered under suction with the help of diatomaceous earth. The filtrate was mixed with methanol up to the concentration of 35% to precipitate fibrous glucan, which was washed with portions of aqueous methanol. The concentration of methanol was increased successively and finally anhydrous methanol was used to dehydrate the material and thereafter the purified fibrous glucan was dried, crushed, and sieved, yielding 8 g of white glucan powder. One gram of the glucan thus obtained was dispersed in 2 liters of physiological saline and after treatment with a high-speed blender for 15 minutes, the fully dissolved glucan solution was filtered under suction with the help of diatomaceous earth. Each 20 ml of the filtrate was poured into ampules, the ampules were sealed, and sterilized at 120°C for 15 minutes.

EXAMPLE 2

Effect on Reticuloendothelial Function by carbon clearance method.

Pelikan ink was injected into the tail vein of mice, 2 and 4 days after the intraperitoneal injection of the glucan and a control substance, zymosan, which is a known polysaccharide having activating effect on the reticuloendothelial system. The blood was drawn from the ophthalmic vein 3, 8, 13, and 18 minutes after injection of the pelikan ink, hemolysed by addition to 0.1% sodium carbonate solution, and concentration of the pelikan ink was measured from the optical density of this solution at 660 nm. The half-life, $t\frac{1}{2}$, was calculated from the optical density and the clearance index, K, was calculated from the following equation:

$$K = (\log C_1 - \log C_2)/T_2 - T_1$$

where $C_1$ and $C_2$ are the concentrations of the pelikan ink at time $T_1$ and $T_2$, respectively.

As shown in FIG., 1, the result of this experiment indicated that the glucan has the action of accelerating the reticuloendothelial function and the degree of this action of 2.5 mg/kg of the glucan was equal to that of 100 mg/kg of zymosan.

EXAMPLE 3

Effect on Phagocytic Activity in vitro

The glucan was adminstered intraperitoneally to mice every other day for three times and macrophages were collected from the peritoneum two days after the last administration. The collected macrophages were mixed with the cells of *Saccharomyces cerevisiae* (ATCC 9763) or of *Candida albicans* (YU 1200), the cells were stained with Giemsa solution 30 minutes later in the case of the former and 8 minutes later in the case of the latter, and the number of macrophages that had phagocytised was calculated.

As shown in FIG. 2, this result indicated that a higher phagocytic rate was found in animals given 0.63–5 mg/kg of the glucan than in control animals in proportion to the dose administered. The phagocytosis was especially marked against *Candida albicans*, the macrophages from the animals given 2.5 mg/kg of the glucan showing over twice the phagocytic rate of the control animals. In other words, acceleration in phagocytic action was observed by the administration of the glucan.

EXAMPLE 4 effect on enzyme activity in intraperitoneal cells.

After intraperitoneal injection of the glucan of this invention, the cells were collected from the peritoneum of mice, 5 to a group, and from untreated control mice, and a cell suspension of $10^7$ cells/ml was prepared. Activity of enzymes was measured with this cell suspension; that of alkaline phosphatase by the method of Fiske and Subbarow, that of $\beta$-glucuronidase by the p-nitrophenylglucuronide method, and that of cathepsin by the method of Cohn and Hirsch based on that of Adams and Smith. Histochemical staining for acid phosphatase and its determination followed the method of Tomonaga, using Naphthol AS-BI phosphate as a substrate. Results (FIGS. 1–4):

1. Activities of acid phosphatase, $\beta$-glucuronidase, and cathepsin in the intraperitoneal exudate cells markedly elevated from a day after the glucan administration, reached a peak after 3–5 days, and returned to the normal level after 15 days. There was no elevation in the activities of alkaline phosphatase and lysozyme.

2. Acid phosphatase staining of the peritoneal macrophages indicated that the cells from mice given the glucan were markedly larger than those from control mice, cytoplasm contained numerous acid phosphatase-positive vacuoles and lysosome granules, and generally showed evidence of functional activation.

These results indicate that administration of the glucan had stimulated the reticuloendothelial cells, and the macrophages showed active phagocytosis and digestive activity. Periodical changes in three enzyme activities of mouse peritoneal cells after intraperitoneal treatment with various amounts of the glucan.

| Dose (mg/kg, ip) | Days after treatment | | | | |
|---|---|---|---|---|---|
| | 3 | 6 | 9 | 12 | 15 |
| | Activity % | | | | |
| a) Acid phosphatase | | | | | |
| Control | 100 | 100 | 100 | 100 | 100 |
| 1.25 | 182 | 171 | 139 | 124 | 105 |
| 2.5 | 180 | 170 | 135 | 117 | 109 |
| 5.0 | 234 | 219 | 140 | 118 | 112 |
| b) $\beta$-glucuronidase | | | | | |
| Control | 100 | 100 | 100 | 100 | 100 |
| 1.25 | 223 | 215 | 200 | 160 | 115 |
| 2.5 | 259 | 254 | 231 | 190 | 156 |
| c) Cathepsin: | | | | | |
| Control | 100 | 100 | 100 | 100 | 100 |
| 1.25 | 141 | 132 | 120 | 107 | 102 |
| 2.5 | 140 | 132 | 129 | 111 | 93 |

EXAMPLE 5

Prevention of Acute Bacterial Infection

In bacterial infectious diseases, those of acute type could not be prevented unless the glucan was administered several days before infection with the bacteria.

The glucan was given intraperitoneally to 10 mice in a group every other day for 3 times and one of the following seven kinds of pathogenic bacteria and one kind of pathogenic fungus were infected 2 days after the last injection of the glucan to observe prolongation in survival.

The microorganisms used were as follows (the number of bacteria or fungus infected in a mouse and the route of administration are given in parentheses):

(1) Staphylococcus aureus 226 ($10 \times 10^8$, ip)
(2) Diplococcus pneumoniae 1-100A ($2 \times 10^3$, ip)
(3) Escherichia coli GN-2411 ($8.8 \times 10^6$, ip)
(4) Salmonella enteritidis 116-54 ($1.25 \times 10^3$, ip)
(5) Pseudomonas aeruginosa H7 ($2 \times 10^6$, ip)
(6) Klebsiella pneumoniae (broth 0.2 ml, ip)
(7) Proteus vulgari (broth × 100, 0.2 ml, ip)
(8) Candida albicans YU-1200 (broth 0.3 ml, ip)
The results of the experiments are as follows:

| Dose (mg/kg) | No. of survival/ No. of mice tested | | | | | | | |
|---|---|---|---|---|---|---|---|---|
| | (1) | (2) | (3) | (4) | (5) | (6) | (7) | (8) |
| 0 (Control) | 0/10 | 0/10 | 0/10 | 1/10 | 0/10 | 0/10 | 0/10 | 0/10 |
| 1.25 × 3 | 10/10 | 1/10 | 5/10 | 3/10 | 2/10 | 9/10 | | 5/10 |
| 2.5 × 3 | 10/10 | 1/10 | 7/10 | 3/10 | 4/10 | 9/10 | | 3/10 |
| 5.0 × 3 | 10/10 | | 9/10 | 3/10 | 9/10 | 9/10 | 4/10 | 5/10 |

The result of intraperitoneal administration of 1.25-5 mg/kg of the glucan is summarized as follows:

a. Marked effect was observed against infection with *Staphylococcus aureus Klebsiella pneumoniae* and *Escherichia coli*.

b. Moderate effect was observed against infection with *Pseudomonas aeruginosa*, *Proteus vulgaris*, and *Candida albicans*.

c. Slight effect or almost ineffect was observed against infection with *Salmonella enteritidis* and *Diplococcus pneumoniae*.

EXAMPLE 6

Combined effect of the glucan and Gentamycin against infection with *Pseudomonas aeruginosa*.

Same as in Example 3, the mice were given intraperitoneal injection of the glucan every other day for three times and, two days after the last injection, a suspension of *Pseudomonas aeruginosa* H7, containing 32 times the number of bacterial cells required for a minimum lethal dose, was injected intraperitoneally. One hour after this infection, Gentamycin was given as a single subcutaneous injection and survival of the mice was examined. As shown in the following table, a marked effect of the combined use of Gentamycin and the glucan was observed.

| Gentamycin alone | | Gentamycin + the glucan | | |
|---|---|---|---|---|
| Dose (mg/kg) | No. of Survival | Gentamycin (mg/kg) | the glucan (mg/kg × 3) | Number of Survival |
| 200 | 1/10 | 200 | 5 | 10/10 |
| 100 | 0/10 | 100 | 5 | 10/10 |
| 50 | 0/10 | 50 | 5 | 10/10 |
| 25 | 0/10 | 25 | 5 | 5/10 |
| 12.5 | 0/10 | 12.5 | 5 | 4/10 |
| Control | 0/10 | 0 | 5 | 0/10 |

EXAMPLE 7

Effect of Route of Administration of the glucan on Acute Bacterial Infection.

Mice were infected with *Escherichia coli* GN-2411 and the same experiments as above were carried out. Results are given in the following table.

| Amount of bacteria infected Route of administration of the glucan Dose (mg/kg) | Broth × 20, 0.3 ml, ip | | | Broth × 10, 0.2 ml, ip | | |
|---|---|---|---|---|---|---|
| | ip* | im | sc | ip | im | sc |
| 2.5 | 1/10 | 1/10 | 1/10 | 0/10 | 0/10 | 0/10 |
| 5.0 | 7/10 | 0/10 | 1/10 | 10/10 | 1/10 | 3/10 |
| 20 | 10/10 | 3/10 | 1/10 | 10/10 | 5/10 | 2/10 |
| 50 | | 6/10 | 1/10 | 4/10 | 4/10 | 6/10 |

*ip = intraperitoneal, im = intramuscular, sc = subcutaneous

Intraperitoneal administration of the glucan showed a significant effect with the least dose, followed by intramuscular administration, and subcutaneous administration required the largest dose of over 50 mg/kg to be effective. This tendency was considered to be due to the difference in the rate of distribution of the glucan in body which is a high molecular substance.

EXAMPLE 8

Treatment of Tuberculosis with the glucan alone or in combination with other antituberculosis agents.

In chronic infections like tuberculosis, administration of the glucan after infection was sufficiently effective. Mice were infected with 0.5 and 1 mg of sensitive strain of *Mycobacterium tuberculosis* Kurono or the human-type strain resistant to isonicotinic acid hydrazide and streptomycin, *M. tuberculosis* Schacht, intravenously. From the day after the infection, the glucan was given intraperitoneally, every other day for 10 times, and streptomycin and ethanbutol were given subcutaneously, every day for 20 days, and the survival of mice was compared in groups with the glucan alone and in those given combined treatment.

a. *M. tuberculosis* Kurono (sensitive human strain). (bacterial dose, 0.5 mg, intravenously)

| Dose (mg/kg) | 50% Survival (days) | 0% survival (days) | Survival over 150 days |
|---|---|---|---|
| None (Control) | 43 | 94 | 0/10 |
| The glucan 5 × 10 (ip) | 100 | 150 | 1/10 |
| Streptomycin 50 × 20 (sc) | 66 | 106 | 0/10 |
| Streptomycin 50 (sc) + The glucan 5 (ip) | 131 | 150 | 2/10 |

As shown above 5 mg/kg (ip) of the glucan and 50 mg/kg (sc) of streptomycin showed approximately the same survival while the combination of these two agents was more effective. The rate of survival in this experiment is shown in FIG. 4.

b. *M. tuberculosis* Schacht (human strain resistant to isonicotinic acid hydrazide and streptomycin)(1 mg, intravenously)

| Dose (mg/kg) | 50% survival (days) | 100 % survival (days) | No. of survival over 98 days |
|---|---|---|---|
| None (Control | 19 | 23 | 0/10 |
| The glucan 2.5 | 33 | 59 | 0/10 |
| The glucan 5.0 | 27 | 87 | 0/10 |
| Ethambutol 10 | 23 | 48 | 0/10 |
| Ethambutol 20 | 50 | 87 | 0/10 |
| Ethambutol 10 + the glucan 2.5 | 55 | >98 | 2/10 |
| Ethambutol 10 + the glucan 5 | 57 | >98 | 3/10 |
| Ethambutol 20 + the glucan 5 | 75 | >98 | 3/10 |

The glucan showed survival effect even against the resistant strain at a intraperitoneal dose of 2.5 and 5 mg/kg, and the effect was approximately the same as 10 and 20 mg/kg subcutaneous dose of Ethambutol. Combined use of these two agents showed increased effect. Rate of survival of the animals in this experiment is shown in FIG. 4.

What we claim is:

1. A method of preventing or treating bacterial infectious diseases which comprises administering to a man or animal in need of said treatment or in need of prevention of bacterial infectious diseases, an antibacterially effective amount of a compound which is a glucan having the following formula:

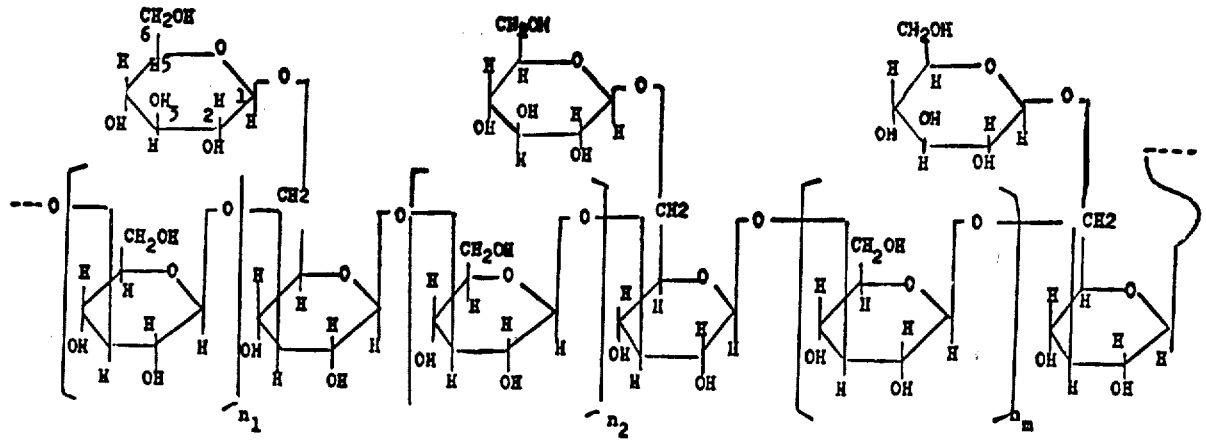

the methylether, the carboxymethylether, the diethylaminoethylether, the acetylester, sulfonylester or phosphorylester thereof wherein each of $n_1 \ldots n_m$ is the number of linearly $\beta - (1-3)$-linked glucose residues, said $n_1 \ldots n_m$ is independently a number from 0 to about 10.

2. The method of claim 1, wherein the composition is administered intraperitoneally, in a dose of 0.001–100 mg/kg/day.

3. The method of claim 1 wherein the composition is administered intramuscularly and the dose is 0.001 – 100 mg/kg/day.

4. The method of claim 1 wherein the composition is administered subcutaneously and the dose is 0.001–100 mg/kg/day.

5. The method of claim 1 wherein the composition is administered intravenously and the dose is 0.001–100 mg/kg/day.

* * * * *